United States Patent [19]

Sytkowski

[11] Patent Number: 5,747,446

[45] Date of Patent: *May 5, 1998

[54] MODIFIED POLYPEPTIDES WITH INCREASED BIOLOGICAL ACTIVITY

[75] Inventor: Arthur J. Sytkowski, Arlington, Mass.

[73] Assignee: Beth Israel Deaconess Medical Center, Boston, Mass.

[*] Notice: The term of this patent shall not extend beyond the expiration date of Pat. No. 5,580,853.

[21] Appl. No.: 756,134

[22] Filed: Nov. 26, 1996

Related U.S. Application Data

[63] Continuation-in-part of Ser. No. 216,259, Mar. 22, 1994, Pat. No. 5,580,853.

[51] Int. Cl.$^6$ .................. A61K 38/16; A61K 38/22; C07K 1/10; C07K 14/505
[52] U.S. Cl. .................. 514/8; 514/12; 514/21; 514/814; 530/397; 530/402; 530/408; 530/409; 530/410; 530/411
[58] Field of Search .................. 530/397, 350, 530/404, 405, 409, 410, 411, 829, 351; 514/8, 12, 21, 814

[56] References Cited

U.S. PATENT DOCUMENTS

| | | | |
|---|---|---|---|
| 4,258,193 | 3/1981 | Fujii et al. | 546/281 |
| 4,659,839 | 4/1987 | Nicolotti et al. | 548/546 |
| 4,677,195 | 6/1987 | Hewick et al. | 514/8 |
| 4,797,491 | 1/1989 | Nitecki et al. | 546/291 |
| 4,904,584 | 2/1990 | Shaw | 435/69.4 |
| 5,024,834 | 6/1991 | Houston et al. | 424/179.1 |
| 5,066,490 | 11/1991 | Neville, Jr. et al. | 421/179.1 |
| 5,112,615 | 5/1992 | Ho et al. | 424/426 |
| 5,116,944 | 5/1992 | Sivam et al. | 530/362 |
| 5,134,071 | 7/1992 | Gaetjens | 435/188 |
| 5,157,123 | 10/1992 | Zora et al. | 546/291 |
| 5,241,078 | 8/1993 | Moreland et al. | 548/542 |
| 5,260,421 | 11/1993 | Chappel et al. | 530/397 |
| 5,580,853 | 12/1996 | Sytkowski | 514/8 |

OTHER PUBLICATIONS

Singh et al., "Comparison of the Cytotoxic Effect of Hormonotoxins Prepared with the Use of Heterobifunctional Cross–Linking Agents . . . " *Bioconjug. Chem.*, (4)6:473–482 (1993).

Peeters et al., "Comparison of Four Bifunctional Reagents for Coupling Peptides to Proteins . . . ", *J. Immunol. Meth.*, 120(1):133–143 (1989).

Pierce, "Pierce 1989 Handbook & General Catalog," *Pierce Europe B.V., NL*, pp. 286–311.

Haniu et al., "Recombinant Human Erythropoietin (rHuEPO): Cross–Linking with Disuccinimidyl Esters and Identification of the Interfacing Domains in EPO," *Protein Science* 2:1441–1451 (1993).

Mayeux et al., "Structure of the Murine Erythropoietin Receptor Complex," *J. Biol. Chem.*, 266(34):23380–23385 (1991).

Jung et al., "Crosslinking of Platelet Glycoprotein Ib By N–Succinimidyl (4–Azidophenyldithio) Propionate and 3,3'–Dithiobis (Sulfosuccinimidyl Propionate)," *Biochimica et Biophysica Acta*, 761:152–162 (1983).

Chamow et al., "Conjugation of Soluble CD4 Without Loss of Biological Activity via a Novel Carbohydrate–Directed Cross–Linking Reagent," *J. Biol. Chem.* 267(22):15916–15922 (1992).

Carlsson et al., "Protein Thiolation and Reverisble Protein–Protein Conjugation," *Biochem. J.*, 173:723–737 (1978).

(List continued on next page.)

*Primary Examiner*—Nancy Degen
*Attorney, Agent, or Firm*—Hamilton, Brook, Smith & Reynolds, P.C.

[57] ABSTRACT

Modified polypeptides with increased biological activity exhibited as either increased potency or prolonged circulating half-life are disclosed with methods of preparing the modified polypeptides and methods of use.

33 Claims, 3 Drawing Sheets

OTHER PUBLICATIONS

Hashida et al., "More Useful Maleimide Compounds for the Conjugation of Fab' to Horseradish Peroxidase Through Thiol Groups in the Hinge," *J. Applied Biochem.* 6:56–63 (1984).

Sytkowski et al., "Isolation and Characterization of an Anti–Peptide Monoclonal Antibody to Human Erythropoietin," *J. Biol. Chem.*, 260(27):14727–14731 (1985).

Lin et al., "Cloning and Expression of the Human Erythropoietin Gene," *Proc. Natl. Acad. Sci. USA*, 82:7580–7584 (1985).

Krystal, G., "A Simple Microassay for Erythropoietin Based on $^3$H–Thymidine Incorporation into Spleen Cells from Phenylhydrazine Treated Mice," *Hematol.* 11(7):649–660 (1983).

McDonald et al., "Cloning, Sequencing, and Evolutionary Analysis of the Mouse Erythropoeitin Gene," *Mol. and Cell. Biol.* 6:842–848 (1986).

Knusli et al., "Polyethylene Glycol (PEG) Modification of Granulocyte–macrophage Colony Stimulating Factor (GM–CSF) Enhances Netrophil Priming Activity but Not Colony Stimulating Activity," *J. of Hemat.* 82:654–663 (1992).

Satake et al., "Chemical Modification of Erythropoietin: An Increase In In Vitro Activity by Guanidination," *Biochimica et Biophysica Acta* 1038:125–129 (1990).

Boissel et al., "Erythropoietin Structure–Function Relationships," *J. Biol. Chem.* 268 (21):15983–15993 (1993).

Powell et al., "Human Erythropoietin Gene: High Level Expression in Stably Transfected Mammalian Cells and Chromosome Localization," *Proc. Natl. Acad. Sci. USA* 83:6465–6459 (1986).

Goldwasser et al., "Purification of Erythropoietin," *Proc. Natl. Acad. Sci. USA* 68(4):697–698 (1971).

Spivak et al., "The In Vivo Metabolism of Recombinant Human Erythropoietin in the Rat," *Blood* 73(1):90–99 (1989).

McMahon et al., "Pharmacokinetics and Effects of Recombinant Human Erythropoietin after Intravenous and Subcutaneous Injections in Healthy Volunteers," *Blood* 76 (9):1718–1722 (1990).

Clark et al., "Disulfide Exchange Between Insulin and its Receptor," *J. Biol. Chem.*, 258(19):11434–11437 (1983).

Clark et al., "Insulin Binding Leads to the Formation of Covalent (—S—S—) Hormone Receptor Complexes," *J. Biol. Chem.*, 257:12239–12344 (1982).

Miyake et al., "Purification of Human Erythropoietin," *J. Bio. Chem.*, 252:5558–5564 (1977).

SPDP
M.W. 312.4
6.8Å

LC-SPDP
M.W. 425.52

Sulfo-LC-SPDP
M.W. 527.56

SMCC
M.W. 334.33
11.6Å

MODIFIED POLYPEPTIDES WITH INCREASED BIOLOGICAL ACTIVITY

RELATED APPLICATIONS

This application is a continuation-in-part of Ser. No. 08/216,259 filed Mar. 22, 1994, now U.S. Pat. No. 5,580,853, the contents of which are hereby incorporated in their entirety.

GOVERNMENT SUPPORT

This invention was made with Government support under Contract No. N00014-90-J-1847 awarded by the Department of the Navy. The Government has certain rights in the invention.

BACKGROUND

Modification of naturally occurring polypeptides which have therapeutic value is often attempted in an effort to increase their biological activity. Several methods have been employed to increase the biological activity of therapeutic proteins. These methods often focus on increasing the size of the therapeutic agents. For example, the size of a protein can be increased through chemical conjugation with a reagent such as polyethylene glycol (PEG) (Knusli, C. et al., *Brit. J. Haematol.* 82:654–663 (1992)). This procedure, also known as "PEGylation", has been reported with several protein agents, first as a means to reduce antigenicity, but also as a way to increase biological activity.

Another method of increasing a protein's size is through chemical cross-linking with another protein. For example, to increase the antigenicity of a protein, chemical cross-linking agents are used to conjugate the immunogenic protein to a carrier molecule such as immunoglobulin or serum albumin.

However, the conjugation of chemical compounds or inert molecules to a polypeptide often results in a significant decrease of the overall biological activity, and of selected biological activity of the polypeptide, (Knusli, C., et al., *Brit. J. Haematol.*, 82:654–663 (1992)). These conjugations must be designed such that the resulting modified polypeptide remains therapeutically efficacious and retains the desired biological properties of the unmodified, wild type (i.e., naturally-occurring) polypeptide (Satake, R., et al., *Biochem. Biophys. Acta.* 1038:125–129 (1990)).

Erythropoietin (EPO) is a glycoprotein hormone involved with the growth and development of mature red blood cells from erythrocyte precursor cells. It is a 166 amino acid polypeptide that exists naturally as a monomer. (Lin, F-K., et al. *Proc. Natl. Acad. Sci. USA* 82:7580–7584 (1985)).

Several forms of anemia, including those associated with renal failure, HIV infection, blood loss and chronic disease can be treated with this hematopoietic growth factor. Erythropoietin is typically administered by intravenous or subcutaneous injection three times weekly at a dose of approximately 25–100 U/kg. Though quite effective, this form of therapy is very expensive. Estimates for the treatment of chronic dialysis patients have ranged from $8,000–10,000 per patient per year.

Another problem encountered in the practice of medicine when using injectable pharmaceuticals is the frequency at which those injections must be made in order to maintain a therapeutic level of the compound in the circulation. For example, erythropoietin has a relatively short plasma half-life (Spivak, J. L., and Hogans, B. B., *Blood,* 73:90 (1989); McMahon, F. G., et al., *Blood,* 76:1718(1990)), therefore, therapeutic plasma levels are rapidly lost, and repeated intravenous administrations must be made. An alternative route of administration is subcutaneous injection. This route offers slower absorption from the site of administration, thus causing a sustained release effect. However, significantly lower plasma levels are achieved and, thus, a similar frequency of injection, as is required with intravenous administration, must be used to get a comparable therapeutic effect.

SUMMARY OF THE INVENTION

The present invention relates to modified polypeptides with increased biological activity, and methods of making these modified polypeptides. Increased biological activity is defined herein as a prolonged plasma half-life (i.e., a longer circulating half-life relative to the naturally occurring polypeptide), or higher potency (i.e., requiring a smaller quantity relative to the naturally occurring polypeptide to achieve a specified level of biological activity). Increased biological activity can also encompass a combination of the above-described activities, e.g., a modified polypeptide with higher potency that also exhibits a prolonged circulating half-life. In any case, because the polypeptides have increased biological activity, the frequency with which they must be administered is reduced, or the amount administered to achieve an effective dose is reduced. In any case, a reduced quantity of modified polypeptide would be necessary over the course of treatment than would be necessary if unmodified polypeptide were used.

Polypeptides encompassed by the present invention include, for example, hematopoietic growth factors such as colony stimulating factors (e.g., G-CSF and GM-CSF), the interleukins (e.g., IL-2 and IL-3), hormones such as basic fibroblast growth factor and glycoproteins such as human follicle stimulating hormone.

More specifically, the present invention relates to modified erythropoietin with increased biological activity, as defined above. The modified erythropoietin of the present invention comprises wild type erythropoietin that has been modified with a heterobifunctional cross-linking reagent. A heterobifunctional cross-linking reagent is defined herein as a reagent with two reactive groups that are capable of reacting with and forming links, or bridges, between the side chains of certain amino acids, between amino acids and carboxylic acid groups, or via carbohydrate moieties. In particular, the heterobifunctional cross-linking reagents used in the present invention contain either a cleavable disulfide bond group or a maleimido group.

The present invention also relates to multimeric erythropoietin comprising two, or more, erythropoietin molecules convalently linked together by one, or more, thioether bond(s). These erythropoietin multimers also exhibit increased biological activity. The present invention further relates to methods of producing the modified erythropoietin polypeptides with increased biological activity described herein, and to methods of their use.

The modification of wild type erythropoietin with a heterobifunctional cross-linking reagent containing a cleavable disulfide bond group resulted in a modified erythropoietin with increased potency relative to unmodified wild type erythropoietin. Importantly, the disulfide bond group can be reduced to a free sulfhydryl group. The availability of a free sulfhydryl group on the erythropoietin polypeptide permitted further modification of erythropoietin to produce multimeric erythropoietin with a prolonged circulating half-life relative to wild type erythropoietin. The production of multimeric erythropoietin was accomplished by a method of chemically cross-linking two, or more, modified erythropoietin polypeptides. Briefly, the method is as follows.

A first erythropoietin derivative was produced by reacting wild type erythropoietin with a heterobifunctional cross-linking reagent containing a cleavable disulfide bond group. The disulfide bond was reduced to produce erythropoietin containing a free sulfhydryl group. A second erythropoietin derivative was produced by reacting wild type erythropoietin with a heterobifunctional cross-linking reagent containing a maleimido group. The first and second erythropoietin derivatives were reacted together, thereby forming at least one thioether bond between the sulfhydryl and maleimido groups, thus forming a homodimer or homotrimer of erythropoietin. Surprisingly, these multimeric erythropoietin molecules exhibit biological activity comparable to wild type erythropoietin. More importantly, the erythropoietin dimers showed a significantly prolonged circulating half-life in vivo, relative to wild type erythropoietin.

Thus, as a result of the work presented herein, erythropoietin has now been modified to produce erythropoietin compositions which exhibit increased biological potency relative to wild type erythropoietin. Moreover, the modified erythropoietin of the present invention can be dimerized and trimerized with other modified erythropoietin molecules to produce multimeric erythropoietin molecules with prolonged in vivo circulating half-lives.

DETAILED DESCRIPTION OF THE INVENTION

Figure 1A:
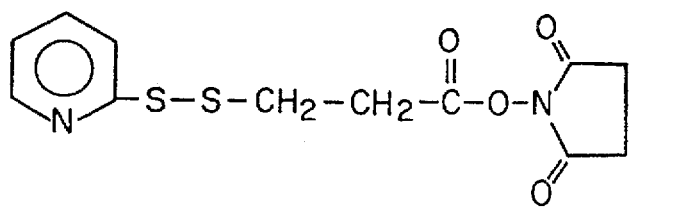
FIG. 1A shows the chemical structure of SPDP.

The present invention relates to modified polypeptides with increased biological activity, and methods of making and using these modified polypeptides. Polypeptides suitable for modification by the methods described herein are polypeptides, preferably monomeric polypeptides, which do not contain any free sulfhydryl groups. Polypeptides of special interest are those polypeptides which interact with a cellular receptor to initiate cellular signaling events, for example, insulin and erythropoietin. Polypeptides encompassed by the present invention are typically used as injectable therapeutic agents. If polypeptides with increased biological activity are used as injectable therapeutic agents, the frequency of administration of these polypeptides can be reduced.

As described herein, these polypeptides can be modified to increase their biological activity relative to the biological activity of the naturally occurring polypeptides. Increased biological activity, is defined herein as a prolonged plasma half-life (i.e., a longer circulating half-life than the naturally occurring polypeptide), or higher potency (i.e., requiring a smaller quantity than the naturally occurring polypeptide to achieve a specified level of biological activity). Increased biological activity, as used herein, can also encompass a combination of the above described activities. For example, a modified polypeptide with higher potency can also have an increased circulating half-life. In any case, because the polypeptides described herein have increased biological activity, the frequency with which they must be administered can be reduced.

The polypeptides encompassed by the present invention are modified with a heterobifunctional cross-linking reagent. The heterobifunctional cross-linking reagent can be attached to one, or more primary amine or amines, within the polypeptide. For example, the heterobifunctional cross-linking reagent can be attached to the amino acid residue, lysine or to the alpha amino terminus of erythropoietin. Alternatively, for glycoproteins, the heterobifunctional cross-linking reagent can be attached to one, or more carbohydrate moiety, or moieties, in an oligosaccharide chain on the polypeptide.

The heterobifunctional cross-linking reagent is generally selected from a group of cross-linking reagents containing either a cleavable disulfide bond group or a maleimido group. The addition of a disulfide bond group to a polypeptide also permits the design of a cross-linking strategy to produce multimeric polypeptides. The disulfide bond can be cleaved by reaction with a known reducing agent, for example, dithiothreitol (DTT) which reduces the disulfide bond in the cross-linking reagent to produce a modified polypeptide derivative containing a free sulfhydryl (SH) group.

A second polypeptide derivative, capable of reacting with a free sulfhydryl group, is then produced by attaching a heterobifunctional cross-linking reagent containing a maleimido group to the naturally occurring polypeptide. Again, the cross-linking reagent can be attached to primary amines or carbohydrate moieties in the polypeptide. The resulting polypeptide derivative containing a maleimido group is reacted with the polypeptide derivative containing a reactive sulfhydryl group resulting in a multimeric polypeptide molecule covalently linked together by at least one thioether bond formed between the SH group and the maleimido group.

Erythropoietin, a glycoprotein hormone involved with the growth and development of mature red blood cells from erythrocyte precursor cells, is a glycosylated polypeptide particularly suited for modification using the methods described herein. Erythropoietin is produced in the kidney in response to hypoxia (e.g., red blood cell loss due to anemia) and regulates red blood cell growth and differentiation through interaction with its cognate cellular receptor. Wild type erythropoietin is defined herein to include recombinant human erythropoietin (Powell, J. S., et al., *Proc. Natl. Acad. Sci. USA*, 83:6465–6469 (1986)), or naturally occurring erythropoietin which has been isolated and purified from blood (Miyake, T., et al. *J. Biol. Chem.*, 252:5558–5564 (1977)) or sheep plasma (Goldwasser, E., et al. *Proc. Natl. Acad. Sci. U.S.A.*, 68:697–698 (1971)), or chemically synthesized erythropoietin which can be produced using techniques well-known to those of skill in the art. Erythropoietin is a 166 amino acid polypeptide that exists naturally as a monomer. (Lin, F-K., et al. *Proc. Natl. Acad. Sci. USA* 82:7580–7584 (1985)). The predicted secondary structure of erythropoietin has been reported (McDonald, J. D., et al., *Mol. Cell. Biol.*, 6:842–848 (1986)).

It was noted from the structure of wild type erythropoietin that the polypeptide does not contain any free (reactive) sulfhydryl (SH) groups. (Boissel, J-P., et al., *J. Biol. Chem.*

268:15983–15993 (1993)). Free SH groups are useful for preparing conjugated proteins, such as radiolabeled antibodies (U.S. Pat. No. 4,659,839), or otherwise chemically modifying the polypeptide resulting in altered biological activity of a polypeptide. A free sulfhydryl group can also play a role in the binding of a polypeptide to its cellular receptor. For example, the polypeptide hormone, insulin, is covalently linked to its cellular receptor via a disulfide exchange mechanism. (Clark, S. and Harrison, L. C., *J. Biol. Chem.*, 258:11434–11437 (1983); Clark, S. and Harrison, L. C., *J. Biol. Chem.*, 257:12239–12344 (1982)). Thus, a free sulfhydryl group can be critical to the biological activity of a polypeptide. Accordingly, a scheme was devised to modify wild type erythropoietin to attach a free sulfhydryl group.

In one embodiment of the present invention, wild type erythropoietin was chemically modified by the covalent attachment of a heterobifunctional cross-linking reagent containing a cleavable disulfide bond group. The cross-linking reagent was attached to a primary amine in the erythropoietin polypeptide. The attachment of a heterobifunctional cross-linking reagent to wild type erythropoietin resulted in erythropoietin with increased potency relative to unmodified erythropoietin.

Figure 1B:
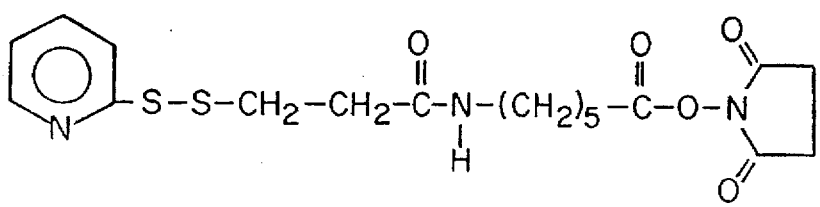
FIG. 1B shows the chemical structure of LC-SPDP.
Figure 1C:
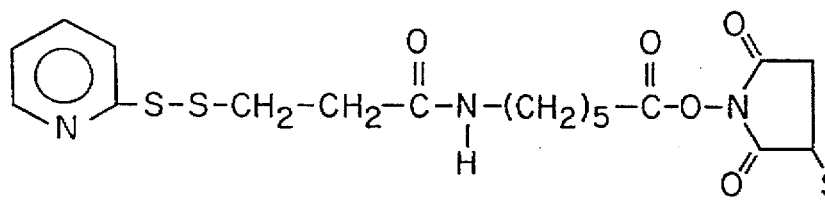
FIG. 1C shows the chemical structure of sulfo-LC SPDP.

Specifically, three different heterobifunctional cross-linking reagents were used to produce modified erythropoietin with increased biological activity. These cross-linking reagents were attached to one, or more, primary amine or amines in the wild type erythropoietin. The cross-linking reagents were N-succinimidyl 3-(2-pyridyldithio) propionate (SPDP), "long chain" N-succinimidyl 3(2-pyridyldithio) propionate (LC-SPDP), wherein the length of the chain of SPDP is increased with additional methyl groups, and sulfonated "long-chain" N-succinimidyl 3(2-pyridyldithio) propionate (sulfo-LC-SPDP) wherein LC-SPDP is sulfonated. SPDP (FIG. 1A), LC-SPDP (FIG. 1B) and sulfo-LC-SPDP (FIG. 1C) are commercially available cross-linking agents (Pierce Chemical Co., Rockford Ill.). SPDP, LC-SPDP and sulfo-LC-SPDP all contain an N-hydroxysuccimmidyl group to react with free amino groups. In addition, these reagents all contain a disulfide bond group that can be further modified to form a reactive sulfhydryl group.

Another heterobifunctional cross-linking reagent that can be used to modify wild type erythropoietin is a carbohydrate specific reagent that attaches to carbohydrate moieties of glycosylated polypeptides. This cross-linking reagent, 3-(2-pyridyldithio) propionyl hydrazide (PDPH), contains an oxidized carbohydrate specific hydrazide and also contains a cleavable disulfide bond group.

Wild type erythropoietin was modified with heterobifunctional cross-linking reagents SPDP, LC-SPDP and sulfo-LC-SPDP as described in detail in Example 1. Briefly, erythropoietin was incubated in the presence of specified concentrations of the chemical reagent N-succinimidyl 3-(2-pyridyldithio) propionate (SPDP) so as to achieve different molar ratios of SPDP:EPO in solution. The unmodified wild type erythropoietin and SPDP modified erythropoietin (SPDP-EPO) were bioassayed according to the method of Krystal, (Krystal, G., *Exp. Hematol.*, 11:649–660 (1983)), which measures the effect of erythropoietin on erythropoiesis in intact mouse spleen cells. The results, shown in Table 1, demonstrate that SPDP-EPO exhibited an increased biological activity relative to the control wild type erythropoietin.

TABLE 1

| SPECIFIC ACTIVITY OF SPDP-MODIFIED ERYTHROPOIETIN | |
|---|---|
| Reaction Mixture, SPDP/EPO, mol/mol | Specific Activity U/mcg |
| 0:1 | 200 + 30 |
| 1:1 | 174 + 20 |
| 3:1 | 340 + 30 |

Erythropoietin modified with sulfo-LC-SPDP (sulfo LC-SPDP-EPO), which has the advantage of increased solubility in aqueous solutions, was also prepared as described in Example 1. Incubation of erythropoietin in the presence of sulfo-LC-SPDP at different molar ratios, followed by dialysis and biological assay revealed that sulfo-LC-SPDP modification of erythropoietin resulted in a 530% increase in potency over the activity of wild type erythropoietin, as shown in Table 2. Thus, the specific activity of the erythropoietin was increased from 170 U/mcg for the wild type erythropoietin to 900 U/mcg for the modified erythropoietin prepared in the presence of 10 fold molar excess of sulfo-LC-SPDP.

TABLE 2

| SPECIFIC ACTIVITY OF SULFO-LC-SPDP MODIFIED ERYTHROPOIETIN | |
|---|---|
| Reaction Mixture, SULFO-LC-SPDP/EPO, mols/mol | Specific Activity U/mcg |
| Experiment #1 | |
| 0:1 | 170 ± 20 |
| 5:1 | 220 ± 30 |
| 10:1 | 900 ± 70 |
| 30:1 | 600 ± 50 |
| 50:1 | 250 ± 30 |
| 100:1 | 350 ± 40 |
| Experiment #2 | |
| 0:1 | 200 ± 30 |
| 1:1 | 200 ± 40 |
| 2:1 | 370 ± 40 |
| 3:1 | 350 ± 40 |
| 6:1 | 380 ± 40 |
| 7:1 | 560 ± 50 |
| 10:1 | 900 ± 60 |

LC-SPDP EPO was also prepared as described in Example 1. Although the biological activity of this derivative was not evaluated, it is reasonable to believe that erythropoietin modified with LC-SPDP would also exhibit increased biological activity due to its close structural relationship to SPDP and sulfo-LC-SPDP.

The chemically modified erythropoietin derivatives described above, which contained a cleavable disulfide bond group, permitted the design of a strategy to cross-link erythropoietin to form EPO-EPO dimers and EPO-EPO-EPO trimers with increased biological activity. These homodimers (EPO-EPO) and homotrimers (EPO-EPO-EPO) are "long-acting" erythropoietin proteins (also referred to herein as LA-EPOs). That is, these multimeric erythropoietin derivatives exhibit a prolonged circulating half-life relative to unmodified, erythropoietin.

The methods of preparing multimeric erythropoietin with increased biological activity are described in detail in Examples 2 and 3. Although erythropoietin is used as the specific example, it is understood that the methods described herein can be used to produce multimers (i.e., a polypeptide covalently cross-linked with one, or more, identical polypeptides) of any suitable polypeptide.

Briefly, a first derivative of erythropoietin was prepared as described in Example 1, by reacting erythropoietin with the compound N-succinimidyl 3-(2-pyridyldithio) propionate (SPDP) to form SPDP-EPO. This reaction introduced an external disulfide bond group into the erythropoietin molecule. To form a free (or reactive) sulfhydryl group, SPDP-EPO can be exposed to a reducing agent, known to those of skill in the art, to reduce the disulfide bond groups. As described in Example 2, SPDP-EPO was exposed to dithiothreitol (DTT), which reduces the disulfide bond in the SPDP moiety to produce an erythropoietin molecule containing free SH groups, also referred to herein as SH-EPO.

Figure 2:
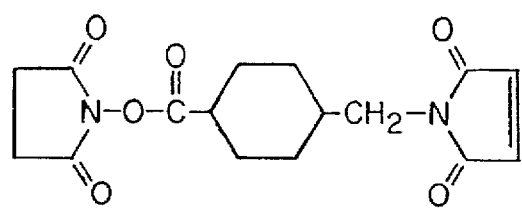
FIG. 2 shows the chemical structure of SMCC.

A second erythropoietin derivative was produced by reacting erythropoietin with succinimidyl 4-(N-maleimidomethyl) cyclohexane-1-carboxylate, also known as SMCC (FIG. 2) to form SMCC-EPO. This reagent has an N-hydroxy succinimidyl (NHS) group at one end and a maleimido group at the other. The NHS group of SMCC reacts with free amino groups in erythropoietin resulting in the formation of SMCC-EPO. The maleimido group of SMCC, now pointing outward from the SMCC-EPO derivative, reacts with free sulfhydryl groups found on SH-EPO. Therefore, when SH-EPO and SMCC-EPO are mixed together in solution, the reactive groups combine resulting in the formation of an EPO-EPO dimer, (i.e., one SH-EPO with one SMCC-EPO) or an EPO-EPO-EPO trimer (i.e., one SMCC-EPO with two SH-EPOs, or two SMCC-EPOs with one SH-EPO) in which the modified erythropoietin polypeptides are covalently linked by at least one thioether bond (e.g., one thioether bond in dimerized EPO and two thioether bonds in trimerized EPO). It is interesting to note that SMCC-EPO, when tested in the Krystal bioassay, did not exhibit any increased biological activity relative to unmodified erythropoietin.

Alternatively, a heterobifunctional cross-linking reagent which contains a maleimido group to attach to carbohydrate moieties such as 4-(4-N-maleimidophenyl) butyric acid hydrazide-HCl (MPBH) and 4-(N-maleimidomethyl) cyclohexane-1-carboxyl-hydrazide-HCl, can be used.

The first and second erythropoietin derivatives were reacted together as described in detail in Example 2. The reaction resulted in the formation of multimeric erythropoietin, as well as unreacted monomeric erythropoietin derivatives, which can be separated by high pressure liquid chromatography (HPLC), as described in Example 2. The erythropoietin dimers comprised two erythropoietin polypeptides linked by one or more thioether bonds. The erythropoietin trimers comprised three erythropoietin polypeptides, also linked by thioether bonds. The trimer can comprise two erythropoietin polypeptides, each containing a free sulfhydryl group which is linked with a third erythropoietin polypeptide containing two or more, maleimido groups. Alternatively, the erythropoietin trimer can comprise one erythropoietin polypeptide containing two, or more, free sulfhydryl groups which is linked with two erythropoietin polypeptides, each containing a maleimido group. The presence of EPO, EPO-EPO dimers and EPO-EPO-EPO trimers was confirmed by Western blot analysis using antibodies specific for erythropoietin as described in Sytkowski, A. J., and Fisher, J. W., *J. Biol. Chem.*, 260:14727–14731 (1985).

Although the monomeric erythropoietin retained its biological activity, the erythropoietin dimers and trimers prepared under the conditions described in Example 2, with SH-EPO, did not exhibit biological activity when tested in the Krystal bioassay. Therefore, a second cross-linking protocol was designed in which a second type of SH-EPO derivative was prepared using sulfo-LC-SPDP. This agent functions similarly to SPDP as outlined above, however, it contains a spacer arm of several angstroms in length (e.g., wherein the number of $CH_2$ groups in the linear portion of the molecule is increased) resulting in increased physical separation of the species attached to its reactive ends. In particular, sulfo-LC-SPDP contains five methyl groups within the linear chain of the molecule, and is also sulfated to increase its aqueous solubility.

Multimeric erythropoietin produced using sulfo-LC-SPDP-EPO (SH-LC-EPO) as the first erythropoietin derivative was prepared, and separated by HPLC as described in detail in Example 2. HPLC fractions containing the trimers, dimers and monomers were tested in the Krystal bioassay for biological activity. Importantly, all three of these species, monomers, dimers, and trimers exhibited biological activity in the Krystal assay. (See FIG. 3).

Multimeric erythropoietin was also produced using heterobifunctional cross-linking reagents containing a free sulfhydryl group attached to the erythropoietin polypeptide and various heterobifunctional cross-linking reagents containing a maleimido group, also referred to herein as "SMCC-like" reagents, as described in detail in Example 3. As used herein, "SMCC-like" reagents are heterobifunctional cross-linking reagents characterized by a N-hydroxy succinimidyl (NHS) group at one end and a maleimido group at the other. As such they act in the same manner as SMCC in that the NHS group of the "SMCC-like" reagents reacts with free amino groups in erythropoietin and the maleimido group of the "SMCC-like" reagents reacts with free sulfhydryl groups. SMCC-like reagents include, e.g., the following: GMBS, γ-maleimidobutyric acid N-hydroxysuccinimide ester; MMBS, m-maleimidobenzoyl-N-hydroxysuccinimide ester; EMCS, ε-maleimidocaproic acid N-hydroxysuccinimide ester; PMPBS, 4-(p-maleimidophenyl)butyric acid N-hydroxysuccinimide ester; and BMPS, β-maleimidoproprionic acid N-hydroxysuccinimide ester. Monomers, dimers and trimers produced with LC-SPDP and the SMCC-like reagents exhibited biological activity as measured in the Krystal assay.

Figure 4:
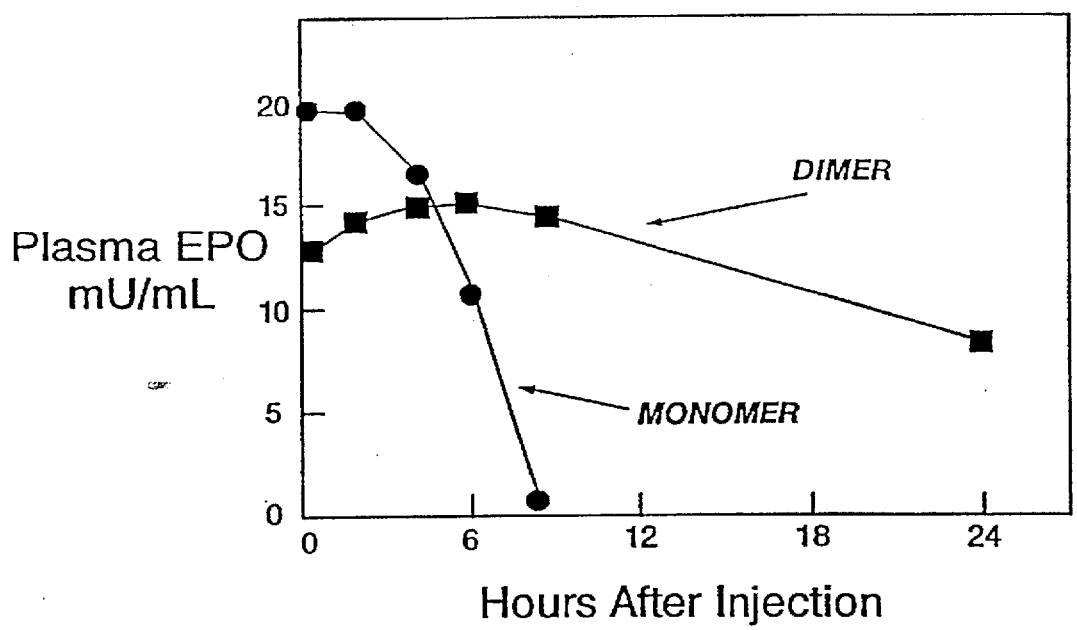
FIG. 4 is a graphic representation of the results of a bioassay demonstrating the increased in vivo half-life of the erythropoietin dimer and monomer.

The circulating half-life in vivo of erythropoietin homodimers was determined as described in detail in Example 4. Monomeric and dimeric erythropoietin was injected into rabbits, and blood samples were analyzed at 5 minutes and 2, 4, 6, 9, and 24 hours after injection. As shown in FIG. 4, the biological activity of dimerized erythropoietin, as measured in the Krystal assay, was still evident 24 hours after the initial injection, whereas the biological activity of monomeric erythropoietin dropped off significantly earlier. Thus, the circulating half-life of dimerized erythropoietin was more than three times longer than wild type erythropoietin. The prolonged circulating half-life of the EPO dimer may be due to its increased size relative to monomeric erythropoietin, which would hinder its excretion from the body through the kidney. Although the erythropoietin trimers were not assayed at this time, it is reasonable to predict that an EPO homotrimer would exhibit similar, or even longer circulatory half-life as the homodimers because a trimer has even greater size than a dimer. These erythropoietin dimers and trimers are also referred to herein as long-acting erythropoietins (LA-EPOs).

Preferred isomers of erythropoietin dimers and trimers can also be prepared. Nine primary amino groups have been identified in the human erythropoietin molecule. At the amino terminus of erythropoietin is an alpha amino group of alanine 1. Additionally, there are eight epsilon amino groups found on lysine 20, 45, 52, 97, 116, 140, 152 and 154. When using LC-SPDP, SMCC, or SMCC-like reagents, one or more of these primary amino groups is/are modified by the reagent.

Variations in the structure of the EPO/EPO dimer could alter the activity/potency of the isoform. Although the three-dimensional structure of EPO is not known, certain regions are held to be important for receptor binding. Since the side chain of lysine, including its epsilon amino group, is hydrophilic, it is expected to be accessible to solvent on the outside of the molecule and, therefore, could take part in EPO receptor binding.

Chemical modification of such a lysine, for example, could decrease activity of the EPO/EPO dimer. Therefore, within the mixture of all possible modifications, it is reasonable to expect that some molecules are less active than others due to such unfavorable linkages. To put it another way, some molecules are more active than others, that is, they are preferred isomers. Another possibility is that steric factors could position the receptor binding domains of the dimer subunits in more favorable steric or less favorable orientations. This could enhance or inhibit the likelihood that both binding domains of each dimer would bind simultaneously.

It is possible to modify amino groups preferentially so as to control isomer structure. Several methods to control (target) modifications of the primary amino groups are described in Example 5.

As a result of the work described herein, modified erythropoietin polypeptides are provided which exhibit increased biological activity. Erythropoietin modified with a heterobifunctional cross-linking reagent containing a cleavable disulfide bond group exhibited a 530% increase in biological activity relative to wild type erythropoietin. This increase in biological activity indicates that an effective amount of modified erythropoietin is substantially less than a comparable effective amount of wild type erythropoietin. The effective amount of modified erythropoietin is defined herein as the amount of erythropoietin required to elicit an erythropoietic response, as indicated by increased growth and/or differentiation of erythrocytic precursor cells. For example, if the typical effective dose of erythropoietin used therapeutically is 25 U/kg, then an effective dose of modified erythropoietin can reasonably be as low as 5.0 U/kg to achieve the same effect.

Alternatively, the effective amount of multimeric erythropoietin described herein, with a prolonged circulating half-life, will require less frequent administration than an equivalent amount of wild type erythropoietin. For example, if an effective dose of erythropoietin is typically administered 3 times a week, multimeric erythropoietin with increased biological activity will only need to be administered once a week. In either case, a reduced quantity of erythropoietin modified with a heterobifunctional cross-linking reagent, or multimeric erythropoietin, will be required over the course of treatment than is necessary if wild type erythropoietin is used.

The modified erythropoietin with increased biological activity described herein can be used in place of wild type erythropoietin whenever treatment with erythropoietin is called for. For example, modified erythropoietin can be used for treatment in an individual experiencing anemia associated with renal failure, chronic disease, HIV infection, blood loss or cancer.

Erythropoietin is generally administered to humans. Effective treatment with erythropoietin requires maintaining a therapeutic blood level. This can be done by continuous administration, that is, by continuous intravenous injections, by discreet intravenous injections, or by subcutaneous injection. The modified erythropoietin of this invention can be employed in admixture with conventional excipients, i.e., pharmaceutically acceptable organic or inorganic carrier substances suitable for parenteral administration that do not deleteriously react with the active derivatives.

Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxymethylcellulose, polyvinyl pyrrolidone, etc.

For parenteral application, particularly suitable are injectable, sterile solutions, preferably oily or aqueous solutions, as well as suspensions, emulsions, or implants, including suppositories.

It will be appreciated that the actual preferred amounts of active compound in a specific case will vary according to the specific compound being utilized, the particular compositions formulated, the mode of application, the particular situs of application, and the organism being treated. Dosages for a given recipient will be determined on the basis of individual characteristics, such as body size, weight, age and the type and severity of the condition being treated.

In addition, the modified erythropoietin of the present invention, with increased biological activity, can be used in any in vitro application in place of wild type erythropoietin. For example, modified erythropoietin can be used in studies of erythropoietin receptor activity. It will again be appreciated that the amount of modified erythropoietin with increased biological activity needed to achieve desired results, (e.g., increased hemoglobinization of red blood cell precursor cells) will be substantially less than the amount of wild type erythropoietin required to achieve those desired results.

The present invention will now be illustrated by the following examples, which are not intended to be limiting in any way.

EXAMPLE 1

SPDP-EPO Derivative with Higher Potency

Three different heterobifunctional cross-linking reagents containing cleavable disulfide bond groups have been used to produce erythropoietin derivatives with increased biological activity. These agents are N-succinimidyl 3-(2-pyridyldithio) propionate (SPDP), "long-chain" N-succinimidyl 3-(2-pyridyldithio) propionate, wherein the length of the chain of SPDP is increased with additional methyl groups (LC-SPDP), and sulfonated "long-chain" N-succinimidyl 3-(2-pyridyldithio) propionate (sulfo-LC-SPDP). Modified erythropoietin polypeptides were prepared as follows.

Recombinant human erythropoietin was produced by expression of the human erythropoietin gene in stably transfected BHK (baby hamster kidney) cells (Powell, J. S. et al., Proc. Nat. Sci. Acad. USA., 83:6465–6469 (1986) and purified using standard laboratory techniques. The purified protein was then incubated in the presence of specified concentrations of the chemical reagent N-succinimidyl 3-(2-pyridyldithio) propionate (SPDP), dissolved in dimethyl sulfoxide, so as to achieve molar ratios of 0:1, 1:1 and 3:1 (SPDP:EPO) in solution. After incubation overnight at room temperature, the solutions were dialyzed against phosphate buffered saline to remove unreacted SPDP.

The wild type erythropoietin and modified erythropoietin (SPDP-EPO) samples were evaluated for biological activity according to the method of Krystal. (Krystal, G., *Exp. Hematol.*, 11:649–660 (1983)). Briefly, the bioassay of Krystal measures the effect of erythropoietin on intact mouse spleen cells. Mice are treated with phenylhydrazine to stimulate production of red blood cell precursor cells in the spleen. After treatment, the spleens are removed, intact spleen cells are carefully isolated and incubated with various amounts of wild type erythropoietin or the modified erythropoietin described herein. After an overnight incubation, $^3$H thymidine is added and its incorporation into cellular DNA is measured. The amount of $^3$H thymidine incorporation is indicative of erythropoietin-stimulated DNA synthesis in erythroid precursor cells via interaction of erythropoietin with its cellular receptor. The results demonstrate that SPDP-EPO exhibited an increased biological activity relative to the wild type erythropoietin, and that this increase in activity was proportional to the molar ratio of SPDP:EPO in the reaction mixture.

Additionally, wild type erythropoietin was modified using sulfo-LC-SPDP, a compound which has the advantage of increased solubility in aqueous solutions. Incubation of erythropoietin in the presence of sulfo-LC-SPDP at the previously described molar ratios followed by dialysis and biological assay revealed that sulfo-LC-SPDP modification of erythropoietin resulted in an increase in potency of approximately 530%. The specific activity of the erythropoietin was increased from 170 U/mcg for the nonderivatized material to 900 U/mcg for the material derivatized in the presence of 10 fold molar excess of sulfo-LC-SPDP.

EXAMPLE 2
Long-Acting Multimeric Erythropoietin Derivatives

To prepare the first SH-EPO derivative, 50 ug of human erythropoietin obtained as described in Example 1, was incubated in the presence of five-fold molar excess of N-succinimidyl 3-(2-pyridyldithio) propionate (SPDP) obtained from Pierce Chemical Company. After incubation at room temperature for sixteen hours, the solution was dialyzed against phosphate buffered saline. The modified erythropoietin was then exposed to 1 mM DTT to reduce the disulfide bond in SPDP resulting in one, or more, free sulfhydryl group(s) on the erythropoietin molecule.

The second erythropoietin derivative, SMCC-EPO, was prepared as follows. A second 50 ug portion of human erythropoietin was incubated in the presence of five-fold molar excess of succinimidyl 4-(N-maleimidomethyl) cyclohexane-1-carboxylate (SMCC). After a sixteen hour incubation at room temperature, the solution was dialyzed against phosphate buffered saline.

The SH-EPO and SMCC-EPO were mixed together in phosphate buffered saline (20 mM sodium phosphate, 150 mM sodium chloride, pH 7.4) at room temperature for 90 minutes, and dialyzed against PBS. The mixture was then subjected to size exclusion HPLC chromatography on TSK 250, in PBS, room temperature, at 1 ml/min. The polypeptides were subjected to SDS polyacrylamide gel electrophoresis, electrophoretic transfer to nitrocellulose, and Western blotting using anti-erythropoietin antibodies according to Sytkowski, A. J., and Fisher, J. W., *J. Biol. Chem.*, 260:14727–14731 (1985). The results showed that the protocol succeeded in the formation of two higher molecular weight species of erythropoietin corresponding to erythropoietin dimers and trimers. However, upon assay in the Krystal bioassay, the erythropoietin dimers and trimers produced with SPDP-SH-EPO did not exhibit any biological activity.

Thus, the protocol was revised to use LC-SPDP-EPO as the first derivative, 50 ug of recombinant human erythropoietin was incubated in the presence of three-fold molar excess of LC-SPDP for sixteen hours at room temperature. The material was then dialyzed and treated with 1 mM DTT resulting in SH-LC-EPO. SMCC-EPO was prepared as described above.

Figure 3:
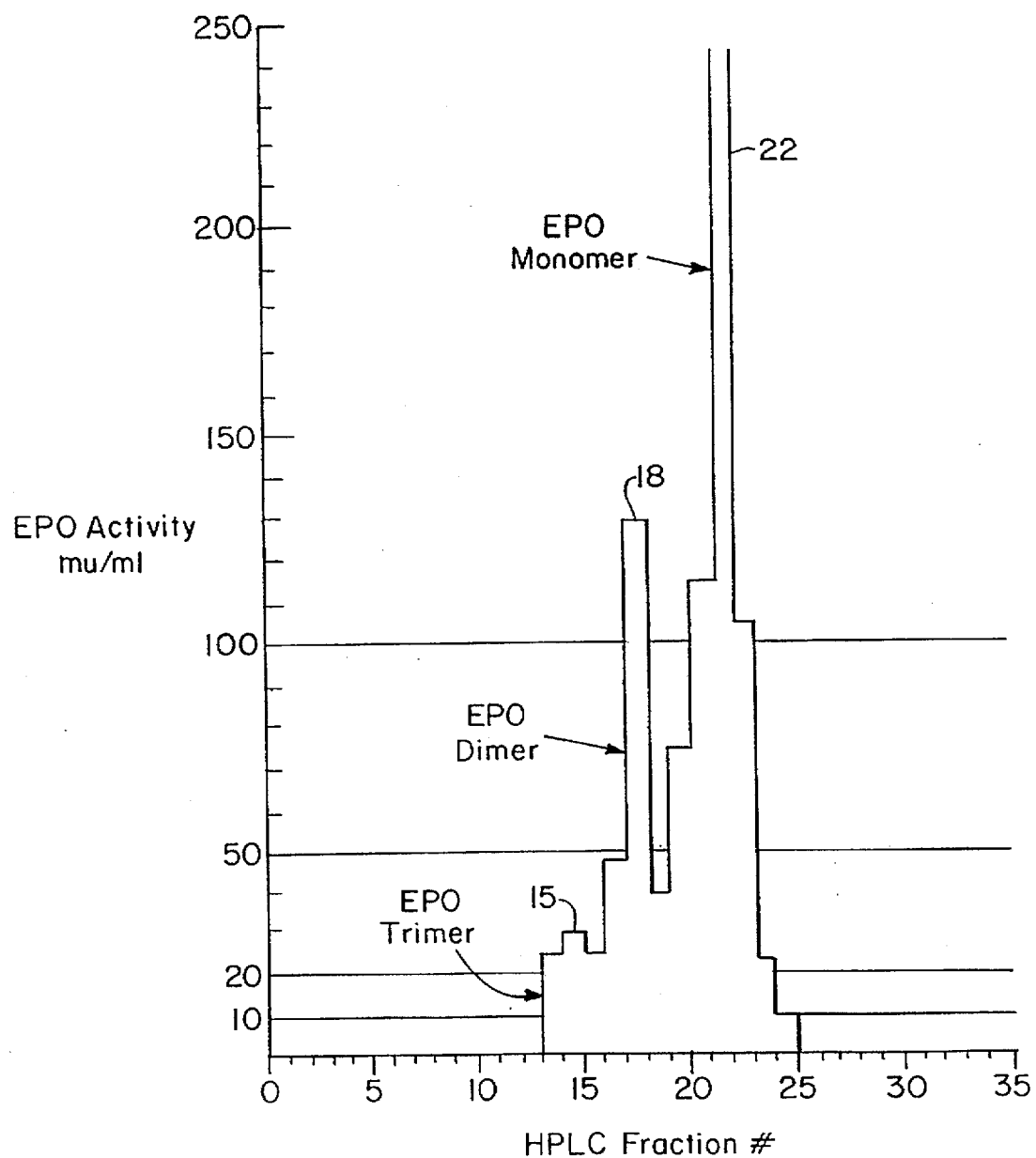
FIG. 3 is a histogram depicting the biological activity of the fractions containing homotrimers, homodimers and monomers of erythropoietin collected after high pressure liquid chromatography (HPLC).

These two species were mixed together in solution and the mixture was subjected to size exclusion HPLC on TSK3000SW. Three erythropoietin protein species were detected with elution times of 10.2, 9.1, and 7.2 minutes respectively. The 10.2 minute elution time was known from previous experiments to be that of wild type erythropoietin monomer. Therefore, the more rapid elution times of 9.1 and 7.2 minutes corresponded to dimers and trimers, respectively. The fractions containing the erythropoietin dimers and trimers were collected and assayed in the Krystal bioassay. Importantly, as shown in FIG. 3, upon testing in the Krystal bioassay, the erythropoietin homodimers and homotrimers exhibited biological activity.

EXAMPLE 3

Crosslinking Erythropoietin Using LC-SPDP and SMCC-Like Reagents

Multimers of erythropoietin were also produced using LC-SPDP-EPO derivatives and EPO derivatives produced by reaction with SMCC-like reagents. The five SMCC-like cross-linking reagents were:

(1) GMBS, γ-maleimidobutyric acid N-hydroxysuccinimide ester;

(2) MMBS, m-maleimidobenzoyl-N-hydroxysuccinimide ester;

(3) EMCS, ε-maleimidocaproic acid N-hydroxysuccinimide ester;

(4) PMPBS, 4-(p-maleimidophenyl)butyric acid N-hydroxysuccinimide ester; and (5) EMPS, β-maleimidoproprionic acid N-hydroxysuccinimide ester.

All of these cross-linking reagents are commercially available, e.g. from Sigma Chemical Co., St. Louis, Mo. The chemical structures of these cross-linkers are shown in Table 3.

TABLE 3

CHEMICAL STRUCTURES OF
"SMCC-LIKE" CROSS-LINKING REAGENTS a. GMBS; γ-maleimidobutyric acid N-hydroxysuccinimide ester;

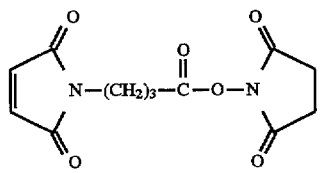

b. MMBS; m-maleimidobenzoyl-N-hydroxysuccinimide ester;

TABLE 3-continued

CHEMICAL STRUCTURES OF "SMCC-LIKE" CROSS-LINKING REAGENTS

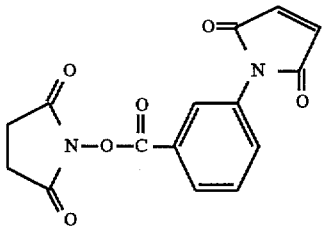

c. EMCS; ε-maleimidocaproic acid N-hydroxysuccinimide ester;

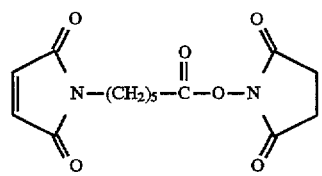

d. PMPBS; 4-(p-maleimidophenyl)butyric acid N-hydroxysuccimide ester;

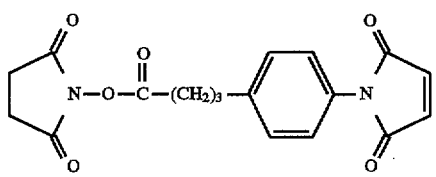

e. BMPS; β-maleimidoproprionic acid N-hydroxysucinimide ester;

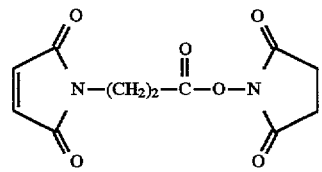

f. SMCC; succinimidyl 4-(N-maleimidomethyl) cyclohexane-1-carboxylate;

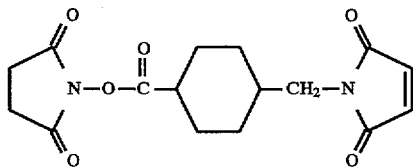

To prepare LC-SPDP, 20 ug of human erythropoietin obtained as described in Example 1, was incubated in the presence of ten-fold molar excess of "longchain" N-succinimidyl 3-(2-pyridyldithio) propionate (LC-SPDP) obtained from Pierce Chemical Company. The incubation occurred in sodium phosphate 20 mM, sodium chloride 100 mM, pH 7.0 (PBS) at 23° C. for 30 min. To stop the reaction, excess PBS at 4° C. was added to the mixture (final volume, 0.5 ml) and then dialyzed for at least 6 h at 4° C. against PBS (3× 1.0 L). Finally, DTT (final concentration, 1 mM) was added to the mixture for 10 min to reduce the disulfide bond in LC-SPDP, resulting in one, or more, free sulfhydryl group(s) on the erythropoietin molecule.

The second erythropoietin derivative, SMCC-like EPO, was prepared as follows. 20 ug portions of human erythropoietin was incubated with a ten-fold molar excess of each of the five SMCC-like reagents listed above and allowed to react. After a 30 min incubation at 30° C. in PBS, the reaction was stopped by adding excess PBS at 4° C. (final volume, 0.5 ml). The mixture was then dialyzed for at least 6 h at 4° C. against PBS (3× 1.0 L).

Equal molar amounts of LC-SPDP EPO and each of the five SMCC-like EPO were placed in five, separate dialysis bags and dialyzed against PBS overnight at 4° C. (1 L). The mixture from each of the dialysis bags was then individually subjected to size exclusion HPLC chromatography. A size exclusion HPLC chromatography column, Progel TSK-3000 $SW_{XL}$ (7.8 mm I.D.×30 cm) and guard column, Progel TSK $SW_{XL}$ (4.0 cm×6.0 mm I.D.) were equilibrated with 100 mM sodium phosphate, 150 mM sodium chloride, pH 7.0. 400 µl (16 µg of total EPO) of monomer/dimer/trimer mixture (e.g. EPO:LC-SPDP+EPO:GMBS) was separated on the equilibrated column at a flow rate of 1.0 ml/min and 0.2 ml fractions were collected. The elution profile was monitored at 280 nm. Bovine serum albumin (final concentration, 2 mg/ml) was added to each fraction to stabilize the dimers/trimers and monomers. Elution profiles of the cross-linked EPO multimers(e.g., EPO:LC-SPDP+EPO:GMBS; EPO:LC-SPDP+EPO:MMBS; EPO:LC-SPDP+EPO:EMCS; EPO:LC-SPDP+EPO:PMPBS; EPO:LC-SPDP+EPO:BMPS; and EPO:LC-SPDP+EPO:SMCC) were similar to those shown in FIG. 3 for EPO:LC-SPDP+EPO:SMCC multimers.

10 µl of each HPLC fraction was diluted in 490 µl of bioassay medium (78% α-MEM, 20% FBS, 0.1 mM β-mercaptoethanol, 1× penicillin/streptomycin/fungizone) and sterilly filtered through 0.2 µm filters. Further final dilutions of 100×, 500× and 5000× were made of the fractions in bioassay medium and assayed for activity using the Krystal in vitro assay, as previously described. Fractions containing monomeric EPO, dimerized EPO and trimerized EPO all exhibited biological activity in the Krystal assay.

Western blot analysis was also performed on the HPLC fractions as follows. 10 µl of each fraction was electrophoresed on a 10% SDS polyacrylamide gel and transferred to nitrocellulose at 25V for 18 h at 4° C. in 25 mM Tris, 192 mM glycine and 10% methanol. The membranes were blocked with 20 mM Tris-HCl, 500 mM NaCl, 0.1% Tween-20 (TBST)+10% Non-fat dry milk overnight with rocking at 4° C. They were then rinsed 2× with TBST, washed 1× for 15 min, 2× for 5 min each, with TBST. The monoclonal EPO antibody AE-7A5 (28 µl Ab in 50 ml TBST/5% dry milk) was placed over the membranes and rocked at 23° C. for 1 h. They were washed as above followed by incubation with goat anti-mouse IgG (Cappel, diluted 1000× in TBST/5% dry milk). Washing was carried out as above with additional 2× for 5 min each. Bands were detected using the ECL detection reagents from Amersham. Equivolumes of solutions 1 and 2 were mixed and 10 ml of the mixture placed over each membrane. After 1 min the membranes were wrapped in Saran Wrap brand plastic wrap and exposed to X-ray film. Fractions containing monomeric EPO, dimerized EPO and trimerized EPO all specifically reacted with the anti-EPO antibodies.

EXAMPLE 4
In Vivo Testing of Multimeric Erythropoietin Derivatives

A group of New Zealand white rabbits were injected intravenously either with wild type monomeric erythropoietin or with dimerized LA-EPO, as prepared in Example 2, at 0.4 mg/ml in PBS. Blood samples were obtained at 5 minutes and 2, 4, 6, 9, and 24 hours and measured the circulating erythropoietin by the Krystal in vitro biologic assay. The results shown in FIG. 4 indicate that the in vivo half-life for monomeric wild type erythropoietin was approximately seven hours, as expected from previously published reports. The in vivo half-life of LA-EPO however, was prolonged beyond the twenty-four hour period of the experiment as shown in FIG. 4.

EXAMPLE 5
Methods of Preparing and Purifying Preferred Isomers of EPO Dimers

Altering the pH of the Reaction

The pKa's of alpha amino groups and of the epsilon amino group are 9.69 and 10.53, respectively, but this is determined for free amino acids in solution. In contrast, when the amino acid is part of a polypeptide, these pKa's can vary greatly due to surrounding structures such as other amino acid side chains. This means that within a given protein such as erythropoietin, each of the epsilon amino groups of the eight lysines can have a different pKa. Lowering the pH of the reaction causes ionization (protonation) of the $NH_2$ group to form a $NH_3^+$ group, thus reducing its reactivity with the succinimidyl moiety of LC-SPDP or SMCC.

Protecting (Blocking) the Amino Group from the Modifying Reagent

A number of means can be used to protect amino acid side chains from chemical modification. For example, site specific antibodies directed toward certain regions of the amino acid sequence could be used. Binding the antibody to the erythropoietin prior to chemical modification would greatly reduce or eliminate modification of those amino groups that form part of the antigenic determinant or are sterically restricted by the bulky immunoglobulin molecule. A series of site specific antipeptide antibodies to erythropoietin covering numerous domains, some of which include lysine residues have been made, as described in Sytkowski, A. J. and Donahue, K. A., J. Biol. Chem, 262:1161 (1987).

In addition to antibody protection, reversible chemical modification of amino groups can be employed. Using this method, the protein is reacted with a reversible modifying reagent such as maleic anhydride. Certain amino groups can be modified, thus preventing subsequent modification when reacted with LC-SPDP, SMCC, or SMCC-like reagents. Following the second modification, the protecting group is removed with an additional chemical reaction at low pH. This method can result in selective modification of unprotected amino groups.

A third means of protecting amino groups is specifically directed toward the alpha amino terminal alanine 1. Instead of expressing the mature EPO protein, the gene can be engineered so that additional amino acid sequence is expressed upstream of alanine 1. This can be engineered so as to include an enzymatic cleavage site immediately upstream of alanine 1. Then, following modification with LC-SPDP or with SMCC, the upstream peptide sequence can be enzymatically cleaved, releasing the mature EPO protein with an unmodified alpha amino group at alanine 1. Side chain targeting due to physicochemical properties and/or physical characteristics of the modifying reagent The physicochemical properties of the modifying reagent can cause it to selectively interact with certain amino groups of the protein. A classic example of this type of effect is seen in the modification of horse liver alcohol dehydrogenase with iodoacetic acid. Reacting the enzyme with iodoacetic acid results in the highly specific modification of cysteine 46, despite the fact that the enzyme contains numerous other free sulfhydryl groups. This specificity is due to the fact that negative charge interacts avidly with a positive charge on the arginyl residue adjacent to cysteine 46. This interaction directs the iodoacetate to this area of the enzyme resulting in a highly selective modification of cysteine 46.

With respect to the modifiers used to produce EPO dimers, the negative charge on sulfo-LC-SPDP or sulfo-SMCC can reasonably similarly direct the modifying reagent to a positive charge. Additionally, nonpolar/hydrophobic moieties in the modifiers such as the cyclohexane portion of SMCC can target the reagent to lysine residues adjacent to hydrophobic nonpolar amino acids.

SH-EPO and maleimido EPO monomers, modified preferentially on certain amino groups, can reasonably result in the production of site specific dimer isomers using the methods of producing dimers described herein. A list of these isomers is presented in Table 4.

TABLE 4

| Production of Site Specific Dimer Isomers | |
|---|---|
| SH-EPO Modified at | Covalently Bonded to Maleimido Modified EPO at |
| Alanine 1 | Alanine 1, lys 20, lys 45, lys 52, lys 97, lys 116, lys 140, lys 152, lys 154 |
| Lys 20 | Alanine 1, lys 20, lys 45, lys 52, lys 97, lys 116, lys 140, lys 152, lys 154 |
| Lys 45 | Alanine 1, lys 20, lys 45, lys 52, lys 97, lys 116, lys 140, lys 152, lys 154 |
| Lys 52 | Alanine 1, lys 20, lys 45, lys 52, lys 97, lys 116, lys 140, lys 152, lys 154 |
| Lys 97 | Alanine 1, lys 20, lys 45, lys 52, lys 97, lys 116, lys 140, lys 152, lys 154 |
| Lys 116 | Alanine 1, lys 20, lys 45, lys 52, lys 97, lys 116, lys 140, lys 152, lys 154 |
| Lys 140 | Alanine 1, lys 20, lys 45, lys 52, lys 97, lys 116, lys 140, lys 152, lys 154 |
| Lys 152 | Alanine 1, lys 20, lys 45, lys 52, lys 97, lys 116, lys 140, lys 152, lys 154 |
| Lys 154 | Alanine 1, lys 20, lys 45, lys 52, lys 97, lys 116, lys 140, lys 152, lys 154 |

In addition to these possible dimer isomers, it is reasonable to expect that favored trimer isomers also can be produced using these methods.

There are several methods that can be utilized to separate and purify the EPO monomers that had been modified selectively as described above. These methods include reverse phase HPLC (RP-HPLC), ion exchange chromatography (e.g., DEAE or CM) and affinity chromatography on immobilized EPO receptor. Each of these are described in detail below.

Reverse Phase HPLC (RP-HPLC)

The combination of linker polarity plus that of the surrounding amino acid sidechains will determine the interaction of the modified EPO monomer with the RP matrix and solvent. This will lead to chromatographically discrete behavior and specifically modified monomers can be isolated.

Ion exchange Chromatography Such as DEAE or CM

Similarly, modification of specific amino groups will alter interaction of the charged EPO with both cation and anion exchangers.

Affinity Chromatography on Immobilized EPO Receptor

EPO receptor protein can be expressed recombinantly, purified and linked covalently to a matrix such as agarose. This affinity matrix can then be used to isolate monomers with the highest affinity for the receptor, and simultaneously to exclude monomers with low or absent receptor binding.

The methods described above for isolation of modified monomers can be applied to dimer and trimer isomers as well. Additionally, size exclusion chromatography is available for isolation of modified dimers and trimers. The different conformation of the dimers and trimers will lead to molecules exhibiting different average stokes radii resulting in differential behavior on high resolution size exclusion HPLC.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A biologically active erythropoietin homodimer comprising two erythropoietin polypeptides covalently linked by at least one thioether bond, wherein:

a) the first erythropoietin polypeptide comprises an erythropoietin polypeptide with a heterobifunctional cross-linking reagent-containing a free sulfhydryl group attached to the erythropoietin polypeptide; and b) the second erythropoietin polypeptide comprises an erythropoietin polypeptide with a heterobifunctional cross-linking reagent containing a maleimido group attached to the erythropoietin polypeptide, wherein said heterobifunctional cross-linking reagent is selected from the group consisting of: γ-maleimidobutyric acid N-hydroxysuccinimide ester, m-maleimidobenzoyl-N-hydroxysuccinimide ester, ε-maleimidocaproic acid N-hydroxysuccinimide ester, 4-(p-maleimidophenyl) butyric acid N-hydroxysuccinimide ester, and β-maleimidoproprionic acid N-hydroxysuccinimide ester, and at least one thioether bond forms between the free sulfhydryl group of the first erythropoietin polypeptide and the maleimido group of the second erythropoietin polypeptide.

2. The erythropoietin homodimer of claim 1 wherein the heterobifunctional cross-linking reagents of a) and b) are attached to one, or more, primary amine or amines in the erythropoietin polypeptides.

3. The erythropoietin homodimer of claim 2 wherein the heterobifunctional cross-linking reagents of a) and b) are attached to a primary amino acid residue selected from the group consisting of: alanine 1; lysine 20; lysine 45; lysine 52, lysine 97, lysine 116, lysine 140, lysine 152 and lysine 154.

4. The erythropoietin homodimer of claim 3, wherein the group of heterobifunctional cross-linking reagents of b) additionally comprises succinimidyl 4-(N-maleimidomethyl)cyclohexane-1-carboxylate.

5. The erythropoietin homodimer of claim 4, wherein the heterobifunctional cross-linking reagent of a) is attached to alanine 1 and the heterobifunctional cross-linking reagent of b) is attached to a primary amino acid selected from the group consisting of: alanine 1, lysine 20, lysine 45, lysine 52, lysine 97, lysine 116, lysine 140, lysine 152 and lysine 154.

6. The erythropoietin homodimer of claim 4, wherein the heterobifunctional cross-linking reagent of a) is attached to lysine 20 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

7. The erythropoietin homodimer of claim 4, wherein the heterobifunctional cross-linking reagent of a) is attached to lysine 45 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

8. The erythropoietin homodimer of claim 4, wherein the heterobifunctional cross-linking reagent of a) is attached to lysine 52 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

9. The erythropoietin homodimer of claim 4, wherein the heterobifunctional cross-linking reagent of a) is attached to lysine 97 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

10. The erythropoietin homodimer of claim 4, wherein the heterobifunctional cross-linking reagent of a) is attached to lysine 116 and the heterobifunctional cross-linking reagent of b) attached to an amino acid selected from the group consisting of: alanine 1, lysine 20, lysine 45, lysine 52, lysine 97, lysine 116, lysine 140, lysine 152 and lysine 154.

11. The erythropoietin homodimer of claim 4, wherein the heterobifunctional cross-linking reagent of a) is attached to lysine 140 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

12. The erythropoietin homodimer of claim 4, wherein the heterobifunctional cross-linking reagent of a) is attached to lysine 152 and the heterobifunctional cross-linking reagent of b) attached to an amino acid selected from the group consisting of: alanine 1, lysine 20, lysine 45, lysine 52, lysine 97, lysine 116, lysine 140, lysine 152 and lysine 154.

13. The erythropoietin homodimer of claim 4, wherein the heterobifunctional cross-linking reagent of a) is attached to lysine 154 and the heterobifunctional cross-linking reagent of b) attached to an amino acid selected from the group consisting of: alanine 1, lysine 20, lysine 45, lysine 52, lysine 97, lysine 116, lysine 140, lysine 152 and lysine 154.

14. The erythropoietin homodimer of claim 1 wherein the erythropoietin is glycosylated erythropoietin and the heterobifunctional cross-linking reagents are attached to one, or more, carbohydrate moiety or moieties in the glycosylated erythropoietin polypeptides.

15. A method of preparing a biologically active erythropoietin homodimer according to claim 1, comprising the steps consisting of:

a) preparing a first erythropoietin derivative by reacting erythropoietin with a heterobifunctional cross-linking reagent containing a cleavable disulfide bond group, under conditions sufficient to introduce the cleavable disulfide bond group into the erythropoietin, thereby producing a first erythropoietin derivative containing a cleavable disulfide bond;

b) cleaving the disulfide bond group contained in the first erythropoietin derivative, thereby producing a first erythropoietin derivative containing a free sulfhydryl group;

c) preparing a second erythropoietin derivative by reacting erythropoietin with a heterobifunctional cross-linking reagent containing a maleimido group, under conditions sufficient to introduce the maleimido group into the erythropoietin, thereby producing a second erythropoietin derivative containing a maleimido group; and d) reacting the first erythropoietin derivative containing a free sulfhydryl group with the second erythropoietin derivative containing a maleimide group, under conditions sufficient to form a thioether bond between the free sulfhydryl group and the maleimido group resulting in the cross-linking of the first and second erythropoietin derivatives, thereby producing modified erythropoietin comprising a first and second erythropoietin derivative.

16. The method of claim 15 wherein the heterobifunctional cross-linking reagents of step a) and step c) react with one, or more, primary amine or amines in the erythropoietin.

17. The method of claim 15 wherein the erythropoietin is glycosylated erythropoietin and the heterobifunctional cross-linking reagents of step a) and step c) react with one, or more, carbohydrate moiety or moieties in the glycosylated erythropoietin.

18. A pharmaceutical composition containing an effective amount of a biologically active erythropoietin homodimer according to claim 1 and a pharmaceutically acceptable carrier.

19. A method of treating anemia in an individual comprising administering to the individual a therapeutically effective amount of a biologically active erythropoietin homodimer according to claim 1.

20. A biologically active erythropoietin homotrimer comprising three erythropoietin polypeptides covalently linked by thioether bonds, wherein:
   a) the first and second erythropoietin polypeptides comprise erythropoietin polypeptides with a heterobifunctional cross-linking reagent containing a free sulfhydryl group attached to each erythropoietin polypeptide; and
   b) the third erythropoietin polypeptide comprises an erythropoietin polypeptide with a heterobifunctional cross-linking reagent containing two, or more, maleimido groups attached to the erythropoietin polypeptide, wherein said heterobifunctional cross-linking reagent is selected from the group consisting of: γ-maleimidobutyric acid N-hydroxysuccinimide ester, m-maleimidobenzoyl-N-hydroxysuccinimide ester, ε-maleimidocaproic acid N-hydroxysuccinimide ester, 4-(p-maleimidophenyl)butyric acid N-hydroxysuccinimide ester, and β-maleimidoproprionic acid N-hydroxysuccinimide ester, and the thioether bonds form between the free sulfhydryl group of the first and second erythropoietin polypeptides and the maleimido groups of the third erythropoietin polypeptide.

21. The erythropoietin homotrimer of claim 20, wherein the heterobifunctional cross-linking reagents of a) and b) are attached to one or more primary amine or amines in the erythropoietin.

22. The erythropoietin homotrimer of claim 21 wherein the group of heterobifunctional cross-linking reagents of b) additionally comprises succinimidyl 4-(N-maleimidomethyl)cyclohexane-1-carboxylate.

23. The erythropoietin homotrimer of claim 22 wherein the heterobifunctional cross-linking reagents of a) and b) are attached to a primary amino acid residue selected from the group consisting of: alanine 1; lysine 20; lysine 45; lysine 52, lysine 97, lysine 116, lysine 140, lysine 152 and lysine 154.

24. The erythropoietin homotrimer of claim 22, wherein the heterobifunctional cross-linking reagent of a) is attached to alanine 1 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

25. The erythropoietin homotrimer of claim 22, wherein the heterobifunctional cross-linking reagent of a) is attached to lysine 20 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

26. The erythropoietin homotrimer of claim 22, wherein the heterobifunctional cross-linking reagent of a) is attached to lysine 45 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

27. The erythropoietin homotrimer of claim 22, wherein the heterobifunctional cross-linking reagent of a) is attached to lysine 52 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

28. The erythropoietin homotrimer of claim 22, wherein the heterobifunctional cross-linking reagent of a) is attached to lysine 97 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

29. The erythropoietin homotrimer of claim 22, wherein the heterobifunctional cross-linking reagent of a) is attached to lysine 116 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

30. The erythropoietin homotrimer of claim 22, wherein the heterobifunctional cross-linking reagent of a) is attached to lysine 140 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

31. The erythropoietin homotrimer of claim 22, wherein the heterobifunctional cross-linking reagent of a) is attached to lysine 152 and the heterobifunctional cross-linking reagent of b) is attached to an amino acid selected from the group consisting of: alanine 1, lysine 20, lysine 45, lysine 52, lysine 97, lysine 116, lysine 140, lysine 152 and lysine 154.

32. The erythropoietin homotrimer of claim 22, wherein the heterobifunctional cross-linking reagent of a) is attached to lysine 154 and the heterobifunctional cross-linking-reagent of b) is attached to an amino acid selected from the group consisting of: alanine 1, lysine 20, lysine 45, lysine 52, lysine 97, lysine 116, lysine 140, lysine 152 and lysine 154.

33. A biologically active erythropoietin homotrimer comprising three erythropoietin polypeptides covalently linked by thioether bonds, wherein:
   a) the first erythropoietin polypeptide comprises an erythropoietin polypeptide with a heterobifunctional cross-linking reagent containing two, or more, free sulfhydryl groups attached to the polypeptide; and b) the second and third erythropoietin polypeptides comprise erythropoietin polypeptides with a heterobifunctional cross-linking reagent containing a maleimido group attached to each polypeptide, wherein said heterobifunctional cross-linking reagent is selected from the group consisting of: γ-maleimidobutyric acid N-hydroxysuccinimide ester, m-maleimidobenzoyl-N-hydroxysuccinimide ester, ε-maleimidocaproic acid N-hydroxysuccinimide ester, 4-(p-maleimidophenyl) butyric acid N-hydroxysuccinimide ester, and β-maleimidoproprionic acid N-hydroxysuccinimide ester, and the thioether bonds form between the free sulfhydryl groups of the first erythropoietin polypeptide and the maleimido group of the second and third erythropoietin polypeptides.

* * * * *